United States Patent
Haberl (10) Patent No.: US 9,504,492 B2
(45) Date of Patent: Nov. 29, 2016

(54) THREE DIMENSIONAL LIFE-SIZE MODEL OF A CHILD'S SKULL AND METHOD USING SAID MODEL

(71) Applicant: Hannes Haberl, Berlin (DE)

(72) Inventor: Hannes Haberl, Berlin (DE)

(*) Notice: Subject to any disclaimer, the term of this patent is extended or adjusted under 35 U.S.C. 154(b) by 124 days.

(21) Appl. No.: 13/753,852

(22) Filed: Jan. 30, 2013

(65) Prior Publication Data

US 2013/0190832 A1 Jul. 25, 2013

Related U.S. Application Data (63) Continuation-in-part of application No. 11/578,822, filed as application No. PCT/EP2005/004361 on Apr. 22, 2005, now Pat. No. 8,388,350.

(30) Foreign Application Priority Data

Apr. 23, 2004 (DE) .................. 10 2004 020 020

(51) Int. Cl.

| | |
|---|---|
| G09B 23/28 | (2006.01) |
| A61B 17/56 | (2006.01) |
| A61F 2/28 | (2006.01) |
| A61F 2/30 | (2006.01) |
| A61B 17/68 | (2006.01) |
| A61B 17/88 | (2006.01) |
| G09B 23/30 | (2006.01) |
| A61B 17/80 | (2006.01) |
| A61B 17/00 | (2006.01) |

(52) U.S. Cl.
CPC .......... *A61B 17/56* (2013.01); *A61B 17/688* (2013.01); *A61B 17/8863* (2013.01); *A61F 2/2875* (2013.01); *A61F 2/30942* (2013.01); *G09B 23/28* (2013.01); *G09B 23/30* (2013.01); *A61B 17/8061* (2013.01); *A61B 17/8085* (2013.01); *A61B 2017/00004* (2013.01); *A61B 2090/0813* (2016.02); *A61F 2002/30706* (2013.01); *A61F 2002/30957* (2013.01); *A61F 2250/0082* (2013.01); *Y10T 29/49* (2015.01)

(58) Field of Classification Search
USPC ....... 434/262, 264, 267, 270, 274, 295–297; 623/17, 19
See application file for complete search history.

(56) References Cited

U.S. PATENT DOCUMENTS

| | | | |
|---|---|---|---|
| 2,988,823 A | 6/1961 | Rosenbloom | |
| 3,009,265 A | 11/1961 | Bezark | |
| 3,802,096 A | 4/1974 | Matern | |

(Continued)

FOREIGN PATENT DOCUMENTS

EP 0720835 7/1996

*Primary Examiner* — Kurt Fernstrom
(74) *Attorney, Agent, or Firm* — 24IP Law Group; Timothy R DeWitt (57) ABSTRACT

The present invention relates to a method for the manufacture of a three-dimensional life-size model of a human child's skull, as well as to methods using the model. The invention provides method for the manufacture of a child's skull within its first year of life. The method comprises the steps of establishing shape characteristics of a child's skull from the group of features including the horizontal curvature of the forehead, the vertical curvature of the forehead, the width of the forehead, the fronto-nasal angle, the fronto-occipital diameter, the biparietal diameter and the horizontal radius of curvature of the occipital module, selecting one or more of the established features and preparing a three-dimensional model of a child's skull or parts from the skull from the selected features.

4 Claims, 11 Drawing Sheets

(56) References Cited

U.S. PATENT DOCUMENTS

| | | |
|---|---|---|
| 4,708,836 A | 11/1987 | Gain |
| 4,773,865 A | 9/1988 | Baldwin |
| 5,156,777 A | 10/1992 | Kaye |
| 5,397,361 A | 3/1995 | Clark |
| 5,941,712 A | 8/1999 | Smith |
| 6,112,109 A | 8/2000 | D'Urso |
| 6,206,703 B1 | 3/2001 | O'Bannon |
| 6,409,516 B1 | 6/2002 | Thill |
| 6,957,961 B1 | 10/2005 | Owens |
| 7,243,888 B2 | 7/2007 | Peek |
| 7,731,499 B2 | 6/2010 | Sze |
| 2002/0164569 A1 | 11/2002 | Dudas et al. |
| 2005/0154292 A1 | 7/2005 | Tank |
| 2006/0154214 A1 | 7/2006 | Miller |

THREE DIMENSIONAL LIFE-SIZE MODEL OF A CHILD'S SKULL AND METHOD USING SAID MODEL

CROSS-REFERENCE TO RELATED APPLICATIONS

The present application is a continuation-in-part of U.S. patent application Ser. No. 11/578,822 filed by the present inventor on Dec. 22, 2006 based upon International Application No. PCT/EP2005/04361 designating the U.S. and claiming priority of German application DE 10 2004 020 020.3 filed Apr. 23, 2004. All of the above applications are incorporated by reference herein in their entirety.

BACKGROUND OF THE INVENTION

1. Field of the Invention

The present invention relates to a method for the manufacture of a three-dimensional life-size model of a human child's skull, as well as to methods using the model.

2. Brief Description of the Related Art

The research into potential corrections of genetic disturbance conditions in the growth of the skull on a cellular level has so far not furnished results useful in practice. Patients suffering from premature cranial suture synostoses (incidence 1:1,000) are therefore dependent on a surgical correction now as before for improvement of their appearance or for a reduction of the risk of functional damage.

The rapid increase of the brain volume throughout the first months in a child's life supports the earliest performance possible of the necessary extensive surgical operation. The age level that is deemed to be most expedient in the sense of risk assessment is stated to be within the range from 4 to 12 months. The necessary operation is extensive and, measured by the age, involves some risks. There is a need for a simplification and shortening of the duration of the operation due to the comparatively high loss of blood.

From the viewpoint of surgical techniques, the methods of bone fragmentation, re-shaping and repositioning have been commonly adopted, which Paul Tessier had proposed (Tessier P. "Total facial osteotomy". Crouzon's syndrome, Apert's syndrome: oxycephaly, scaphocephaly, turricephaly. Ann. Chir. Plast. 1967; 12(4): pp. 273 to 286). The surgical technique and the time of operation have been varied by various authors throughout the years then following (Renier D, Lajeunie E, Arnaud E, Marchac D. "Management of craniosynostoses". Childs Nerv. Syst. 2000; 16(10 to 11): pp. 645 to 658). In this manner, a certain standardization of the conventional techno-methodological approach could be observed in the course of the past 30 years.

As a matter of fact, however, some important and time-consuming aspects of the surgical operation have so far not been addressed by trend-setting discussions:

1. The criteria of a precise shape "target" are missing. Without planning criteria, the most important and frequently only indication of the surgical operation—i.e. the most perfect approximation possible to the fictitious "healthy" shape of the skull of the patient—remains left to the operating surgeon's sense of shape or his or her arbitrary aesthetic criteria. The duration of the operation may be prolonged by corrections, which are required again and again in the sense of groping for the optimum shape. On account of the individual shape, an objective check of the success is almost precluded.

2. Due to the rigidity of the material, the selection of the shape and the realization in the region of calotte sections presenting different degrees of curvature, for instance in the zone of the forehead, involve a high level of difficulty for the skilled operating surgeon, too.

They are lengthy and wearisome, furnishing sub-optimum results on at least one level rather frequently. Thus, there is a need to provide means, which enable and facilitate the correction of a child's head malformation to obtain a mostly individual readjusted shape of the malformed parts of the skull.

The objective of the present disclosure is to provide a method for the manufacture of a model of a child's skull within the first year of a child's life. A further objective of the invention aims at solving the problems in terms of surgical techniques for re-shaping the skull in the case of congenital or acquired cranial deformations.

A further problem underlying the present invention was the provision of tools and a method for their manufacture for improving and simplifying surgical reconstructions of the skull in the first year of a child's life.

SUMMARY OF THE INVENTION

These problems are solved by the embodiments of the independent claims.

The invention provides method for the manufacture of a child's skull within its first year of life. The method comprises the steps of establishing shape characteristics of a child's skull from the group of features including the horizontal curvature of the forehead, the vertical curvature of the forehead, the width of the forehead, the fronto-nasal angle, the fronto-occipital diameter, the biparietal diameter and the horizontal radius of curvature of the occipital module, selecting one or more of the established features and preparing a three-dimensional model of a child's skull or parts from the skull from the selected features. The three-dimension life-size model of a child's skull shall comprise at least one of a frontal part (frontal module), a parietal part (parietal module) and an occipital part (occipital module), which is characterized by the feature that it is sterilizable or disposable.

The term "sterilizable" as used herein is meant to denote the fact that the model is capable of resisting temperatures and pressures and/or the influences of gas, which are employed usually when a set of surgical instruments, medical equipment for application on a patient and in the interior of a patient's body, etc. are autoclaved or sterilized without causing any damage, specifically deformation, on the model by such a sterilization process. The model is preferably made of an appropriate material suitable to this end, for instance steel, titanium or synthetic resin.

The term "disposable" designates means, which are intended for a one-time use and will be provided sterilized. It is also within the scope of the invention to provide a set of disposable means, e.g. parts of a skull, for their selection and individually adapted combination with regard to the patients shape of skull.

According to one embodiment, provisions are made for the use of only one part or the connection of at least two parts in the model to each other, which are selected from the frontal part, parietal part and occipital part, it being preferred that the parietal part and the occipital part are connected to each other so as to form a parietal and occipital part (parieto-occipital module).

One embodiment envisages that the disclosed three-dimensional model includes additionally a base part (base module) on which the frontal part, parietal part and the occipital part can be arranged.

One embodiment provides for the inventive three-dimensional model constituting an average child's skull, with the average being related to a normal distribution within the first year of a child's life, especially the population of children in the age group of 4 to 12 months and 12 to 20 weeks may be of particular interest.

A further embodiment proposes that the inventive three-dimensional model represents an average child's skull, with the average being related to a normal distribution within the population of children in the age group of 24 to 32 weeks.

It is intended that, with respect to one or several of the features selected from the group including the horizontal curvature of the forehead, the vertical curvature of the forehead, the width of the forehead, the fronto-nasal angle, the fronto-occipital diameter, the biparietal diameter and the horizontal radius of curvature of the occipital module, to prepare a child's skull from the selected features, wherein the inventive model may represent an average child's skull.

One embodiment provides for the feature that, with respect to one or several of the features selected from the group including the horizontal curvature of the forehead, the vertical curvature of the forehead, the width of the forehead, the fronto-nasal angle, the fronto-occipital diameter, the biparietal diameter and the horizontal radius of curvature of the occipital module, the inventive three-dimensional model is located on a percentile curve representing .ltoreq.10%, relative to a normal distribution within the population of children in the age group of 0 to 1 year, it being preferred that it is located on a percentile curve representing 3%.ltoreq.x %.ltoreq.10%, preferably 3%.

Another embodiment provides that, with respect to one or several of the features selected from the group including the horizontal curvature of the forehead, the vertical curvature of the forehead, the width of the forehead, the fronto-nasal angle, the fronto-occipital diameter, the biparietal diameter, the horizontal radius of curvature of the occipital module, the inventive three-dimensional model is located on a percentile curve representing 10%<x %.ltoreq.30%, relative to a normal distribution within the population of children in the age group of 0 to 1 year.

According to another embodiment, it is proposed that, with respect to one or several of the features selected from the group including the horizontal curvature of the forehead, the vertical curvature of the forehead, the width of the forehead, the fronto-nasal angle, the fronto-occipital diameter, the biparietal diameter, the horizontal radius of curvature of the occipital module, the inventive three-dimensional model is located on a percentile curve representing 30%<x %.ltoreq.70%, relative to a normal distribution within the population of children in the age group of 0 to 1 year, it being preferred that it is located on a percentile curve representing 45%.ltoreq.x %.ltoreq.55%, relative to a normal distribution within the population of children in the age group of 0 to 1 year, wherein it is particularly preferred that it is located on a percentile curve representing 50% relative to a normal distribution within the population of children in the age group of 0 to 1 year.

One embodiment provides for the feature that, with respect to one or several of the features selected from the group including the horizontal curvature of the forehead, the vertical curvature of the forehead, the width of the forehead, the fronto-nasal angle, the fronto-occipital diameter, the biparietal diameter, the horizontal radius of curvature of the occipital module, the inventive three-dimensional model is located on a percentile curve representing 55%<x %.ltoreq.70%, relative to a normal distribution within the population of children in the age group of 0 to 1 year.

According to another embodiment provisions are proposed for the feature that, with respect to one or several of the features selected from the group including the horizontal curvature of the forehead, the vertical curvature of the forehead, the width of the forehead, the fronto-nasal angle, the fronto-occipital diameter, the biparietal diameter, the horizontal radius of curvature of the occipital module, the inventive three-dimensional model is located on a percentile curve representing 70%<x %.ltoreq.90%, relative to a normal distribution within the population of children in the age group of 0 to 1 year.

According to another embodiment, the feature is provided that, with respect to one or several of the features selected from the group including the horizontal curvature of the forehead, the vertical curvature of the forehead, the width of the forehead, the fronto-nasal angle, the fronto-occipital diameter, the biparietal diameter, the horizontal radius of curvature of the occipital module, the inventive three-dimensional model is located on a percentile curve representing 90%<x %.≤97%, relative to a normal distribution within the population of children in the age group of 0 to 1 year, it being preferred that the inventive three-dimensional model is located on a percentile curve representing 97%, relative to a normal distribution within the population of children in the age group of 0 to 1 year.

One embodiment provides for the feature that the inventive three-dimensional model is located on the respective percentile curve within the first year of a child's life, wherein the age range of children of 12 to 20 weeks may be of particular interest.

According to another embodiment, provisions are made for the inventive three-dimensional model being located on the respective percentile curve within the age range of children of the age of 24 to 32 weeks. As an age between the fourth and twelfth month seems to be the optimal life span for the correction of a malformed skull, the disclosed method for the manufacture of a child's skull relates particularly to a three-dimensional model of a child's skull within this range.

It is preferred that the exterior dimensions of the inventive three-dimensional model are reduced by 1 to 5 mm in correspondence with the thickness of the bone of a child's skull. The respective value may vary within the indicated range from one patient to the next.

One embodiment provides the feature that the inventive three-dimensional model comprises a molding shell which rests detachably on an interior supporting element, it being preferred that the molding shell includes the frontal part (frontal module), the parietal part (parietal module) and the occipital part (occipital module), which modules are connected to each other in a particularly preferred manner.

One embodiment provides for the feature that the interior supporting element is a structure or a frame on which the molding shell rests.

According to one embodiment provisions are made such that the exterior surface of the molding shell comprises recesses for receiving stabilizer elements, it being preferred that the recesses are apertures in the molding shell, preferably strip-shaped and/or punctiform apertures.

One embodiment proposes the feature that the recesses are disposed on the exterior surface of the molding shell at regular distances from each other.

Provisions are made in one embodiment that the molding shell comprises recesses permitting a connection of stabilizer elements applied on the exterior surface of the molding shell and/or in die recesses to bone plates applied on the molding shell equally from the outside, it being preferred that the connection is realized by means of screwing or riveting, wherein it is particularly preferred that the recesses mentioned last are completely or partly identical with the recesses mentioned before.

The problems underlying the invention are equally solved by a three-dimensional model according to the present invention for application in a method of surgical treatment of a cranio-synostosis.

The objectives of the invention are furthermore reached by a kit comprising at lest one, preferably at least two, most preferably at least three different models according to the present invention, it being preferred that the kit includes five, preferably six, different models according to the present invention.

One embodiment provides for the feature that the kit furthermore comprises one or several parts selected from the following group:

absorbable stabilizer elements, in particular plates or strips suitable for stabilizing cranial bone fragments, absorbable screws and/or rivets for fixing cranial bone fragments on said stabilizer elements, tools for screwing in and/or removing said screws or rivets, in particular screwdrivers and screw removers.

It is preferred that the absorbable stabilizer elements are moldable in a heated condition, it being particularly preferred that the absorbable stabilizer elements are absorbable plates or strips made of lactic acid.

Such absorbable plates or strips made of lactic acid are commercially available.

Provisions are made in one embodiment for the feature that the plates or strips present a physiologically acceptable thickness, width and length, with one kit containing plates and strips of uniform size or of different sizes.

The dimensions of the plates and strips must preferably be selected in consideration of each patient. It is envisaged that the kit preferably contains plates and/or strips of different sizes so as to permit due consideration of the respective individual conditions on the respective site of operation.

The problems underlying the invention are equally solved by an inventive kit for use in a method of surgical treatment of a cranio-synostosis.

The objectives of the invention are furthermore achieved by a method of surgical treatment of a cranio-synostosis on a patient, comprising the following steps:

rendering a three-dimension model according to the present invention available under sterile conditions, which, after comparative measurement, is found to be of closest similarity to the patient, removing a dysplastic calotte section affected by cranio-synostosis and dividing the calotte section into fragments, preferably strips, molding the fragments of the dysplastic calotte section onto the three-dimensional model by thinning, destabilization and/or modeling, fixing the fragments with stabilizer elements, which are known to a person skilled in the art, there below, preferably by screwing and/or riveting, thus forming an implant consisting of fragments and stabilizer elements, implanting the implant by fitting and fixing, preferably screwing, in the patient's skull.

It is preferred that the exterior dimensions of the three-dimensional model are reduced by 1 to 5 mm in correspondence with the thickness of the bones so as to permit an implantation of the re-shaped bone fragments in due consideration of the shape.

One embodiment provides the feature that, for molding the fragments of the dysplastic calotte section, these fragments are placed on the three-dimensional model and are maintained in their position by the application of force, preferably by means of a reversibly removable fixing means, preferably using a resilient tape.

It is preferred that the implant is lifted off the three-dimensional model for implantation An essential starting point of the invention resides in the translation of a new method of statistical modeling into practical application, which method is the first to offer valid data on the normal distribution of the shapes of children's heads. The inventors surprisingly found that it is possible to employ an appropriate three-dimensional model individualized for and matched with the respective patient, which can be sterilized, so as to achieve good results in a plannable and rationally reproducible manner.

For preparation, typical shape characteristics (horizontal curvature of the forehead, vertical curvature of the forehead, the width of the forehead, fronto-nasal angle, fronto-occipital diameter, biparietal diameter, horizontal radius of curvature of the occipital square etc.) within the first year of a child's life are established and analyzed. The group of reconstructions of individuals healthy in terms of growth of the skull from the age levels between 12 to 20 weeks (4 months) and 24 to 32 weeks (8 months) are of particular interest. On principle, all measured values are documented in percentile curves. A percentile curve as used herein serves as reference of a respective patient against other patients of the same age. A 10% percentile means that, with respect to a certain characteristic, 9% of the patients of the same age group are to be found below the value of the patient under examination and 90% of the patients in the same age group are to be found above the value of the patient under examination with respect to the same characteristic. By fusing the reconstructions or the selected features of a skull of children of identical age, a virtual average head corresponding to defined time points may be constructed like a skull for each month or "months" or "8 months" (.about.50% percentile) and one head each with maximum deviations in shape of individual characteristics (length of the head, width of the head, width of the forehead, curvature of the forehead, etc.) (.about.3% percentile or .about.97% percentile) is computed and converted into stereo lithographic models. The entire width of variations of different features should be included as far as this is possible. Thus, it is possible to construct a skull corresponding to the age of a child when the correction its skull shall take place.

Roughly 6 varying partial models are envisaged for each calotte section per age group, which may then be chosen in consideration of the patient's given shape of the head and of the desired modification.

Compared against the screen-bound surgical planning methods so far common, it is now possible to avoid the generation of costs (and risks) by individualized imaging and to permit the precision in the conversion of the specifications of shape without the application of image-dependent navigation systems, for example.

To this end, a set of instruments is developed from the data pool, based on an age-related set of three-dimensional multi-part shape modules. Dysplastic calotte sections may then be precisely re-shaped over a matching inventive model, using pre-shaped absorbable stabilizer elements, rigidified on the interior side and re-implanted as one block.

The application of an inventive model or of several inventive models permits the replacement of the sub-optimal transposition of fragments by the actual multi-dimensional re-shaping, with a correction of the radii of curvature, on a shaping surface.

A particular advantage of this method moreover resides in the position of the comparatively thick absorbable stabilizer elements on the interior side, which is more expedient from a cosmetic point of view.

This result can now be planned by application of the inventive surgical concept or the inventive three-dimensional models or kits, respectively, which are proposed here; by reference to the starting model of the operation, the result can be controlled at any point of time. Correction losses caused by pathologic bone growth may be quantified and may be taken into consideration into the specifications for the operation (model planning) on a long-term basis. The number of sub-optimal results and the frequency of repeated operations are thus reduced cases of non-syndromal synostosis.

BRIEF DESCRIPTION OF THE DRAWINGS

For a more complete understanding of the present invention and the advantages thereof, reference is now made to the following description and the accompanying drawings, in which.

PREPARATORY WORK FOR STATISTICAL MODELING

The generation of 3D atlases and their use for 3D-shape analysis is presently the subject matter of research in various fields such as the anthropometry, the image analysis in medicine and ergonomic studies. A 3D atlas describes the average shape of an object and its typical variations within a given sample. The creation of an atlas requires the comparison of shapes, with a distinction being made between surface-based and volume-based approaches. The result of the comparison of shapes permits the displayability of the sample in a highly dimensional vector space. There are quite a number of methods of extracting pertinent statistical parameters in the literature, which are used to create a specific atlas.

The generation of the surface models for the 3D atlas requires segmentation (classification of tissues) of tomographic imaging data. Software systems supporting the segmentation process by means of manual and semi-automatic tools (Analyze, Amira, Materialise) are available to this end.

A promising approach towards the fully automated segmentation is based on the utilization of a priori knowledge in the form of 3D atlases. The atlas is initially created on the basis of the segmented data. As soon as it is constituted by a sufficient number of models it may also be used as such for segmentation, which facilitates and accelerates the segmentation process. The ongoing enlargement of an atlas is required in order to be able to make statements about the general shape of an object with a defined probability.

Description of a Preferred Embodiment of the Inventive Surgical Method Using Inventive Models Following the completed generation of statistical models, 5 to 8 representative variants of shapes are produced for a specific age group (e.g. 4 months). The model most similar to the individual patient after comparative measurements is made available in sterile condition in the operating theater. It is obvious for a person ordinary skilled in the art that the model may be sterilisable or disposable in order to provide a sterile model.

Figure 1A:
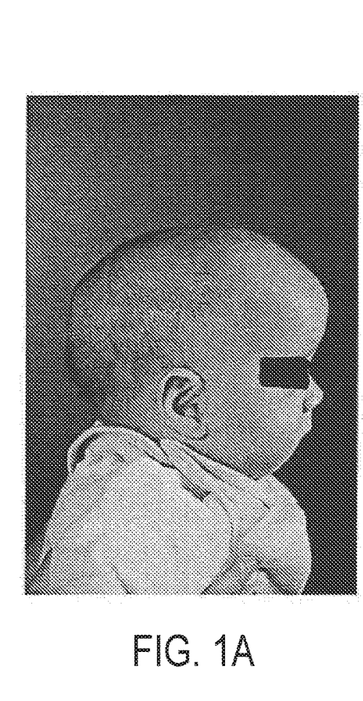
FIGS. 1A and 1B show an example of a baby, 4 months old, suffering from a synostosis along the sagittal suture (FIG. 1A), and the condition four weeks after (FIG. 1B) surgical re-shaping.
Figure 1B:
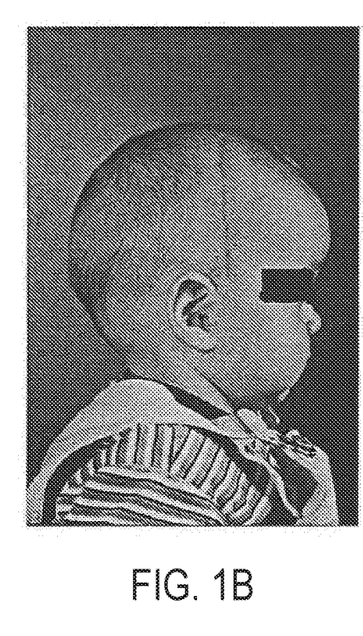
Figure 2A:
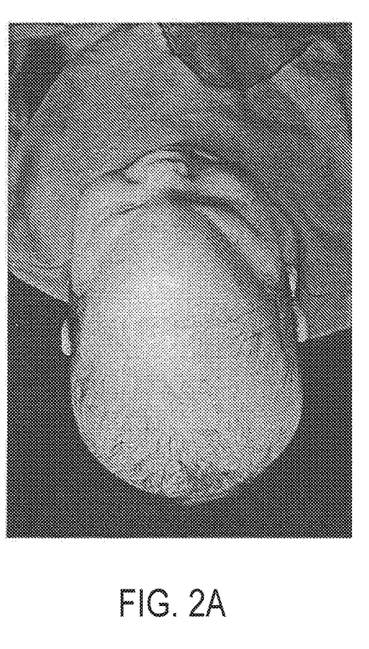
FIGS. 2A and 2B show the example of a baby, 5 months old, suffering from synostosis along the frontal suture (FIG. 2 A), and the condition four weeks after (FIG. 2 B) surgical re-shaping.
Figure 2B:
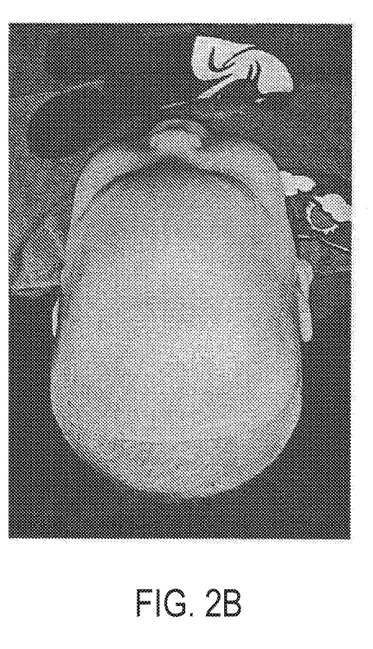
Figure 3A:
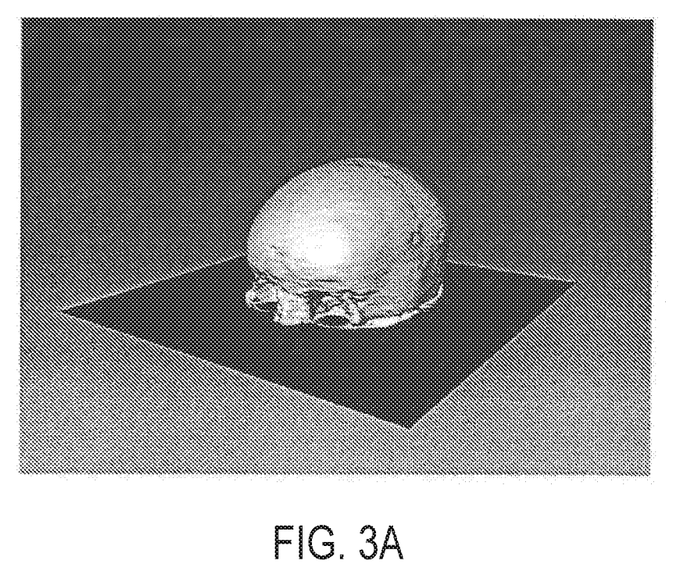
FIGS. 3A to 3C are views of the manual segmentation of a child's cranial calotte from a set of MRT data (magnetic resonance tomography)
Figure 3B:
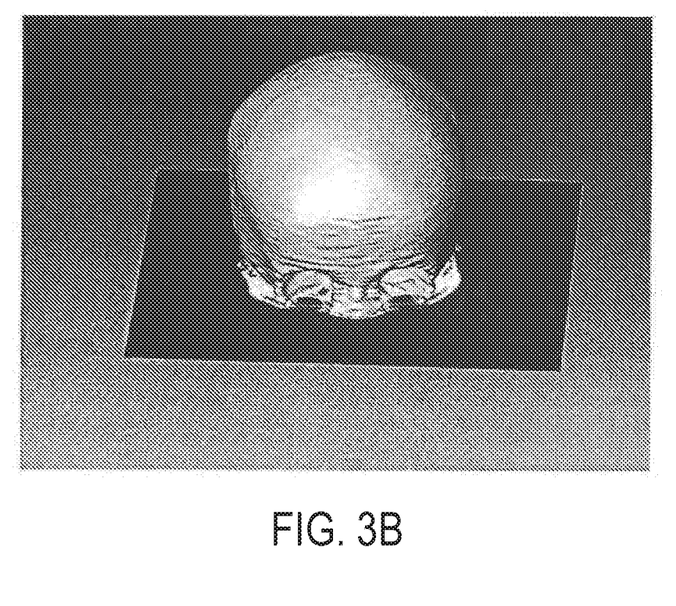
Figure 3C:
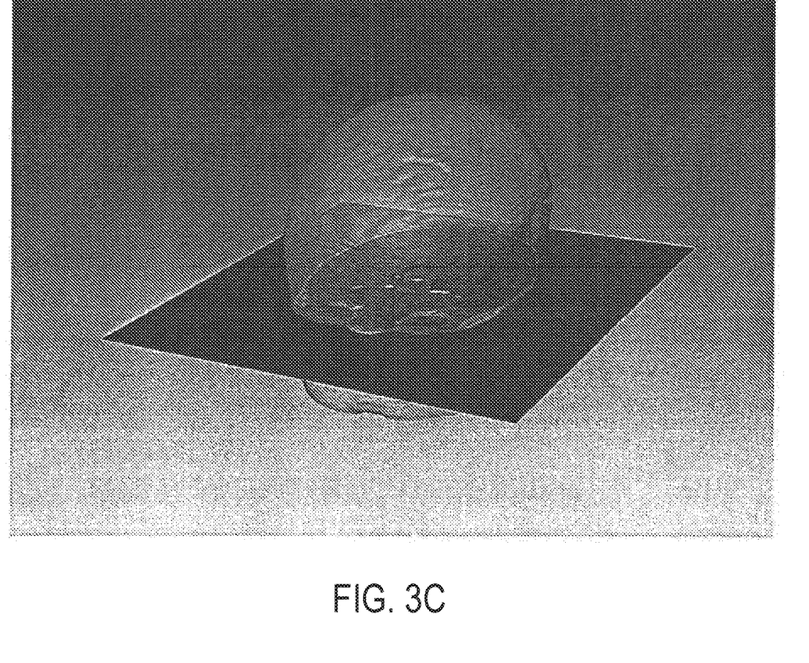
Figure 4:
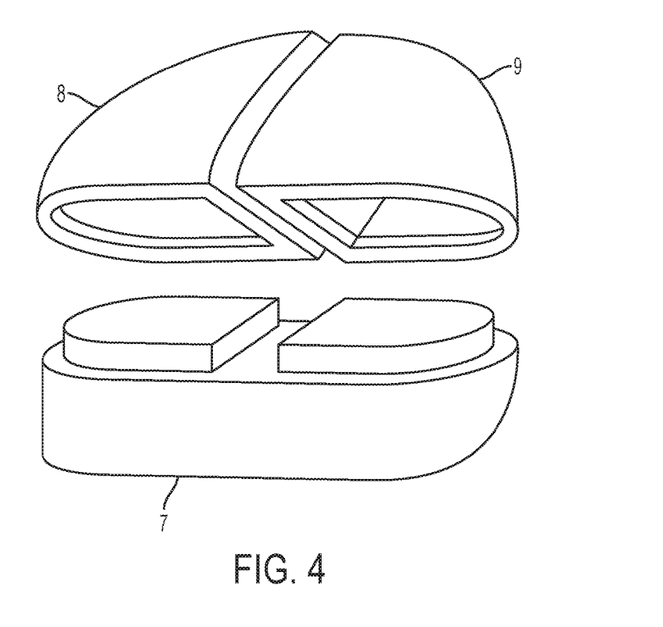
FIG. 4 shows an example of a sterilizable model of a cranial calotte, having a base module 7, a frontal module 8 and a parieto-occipital module 9.
Figure 5:
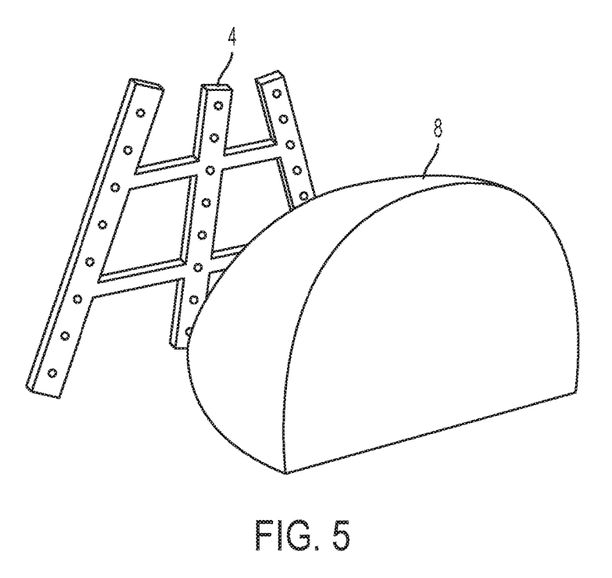
FIG. 5 illustrates the molding of a thermally pliable absorbable stabilizer element 4 onto a frontal module 8.

Now stabilizer elements 4 (e.g. absorbable plates made of lactic acid), which are moldable in heated condition and are preferably absorbable, are then placed onto the model reduced already by the calotte diameter and the diameter of the plate. (FIG. 5).

Figure 6:
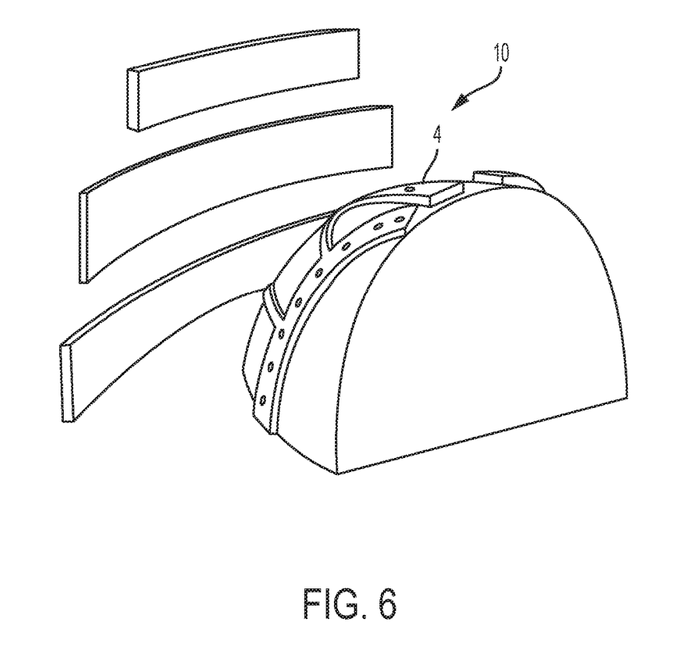
FIG. 6 shows the molding of a destabilized bone strip 10 onto the cured stabilizer element 4 over a frontal module.

After the molding elements have been cured the dysplastic calotte section 10, divided into bone strips, is molded onto the model. To this end, the individual fragments 10 are thinned, destabilized and modeled (FIG. 6).

Figure 7:
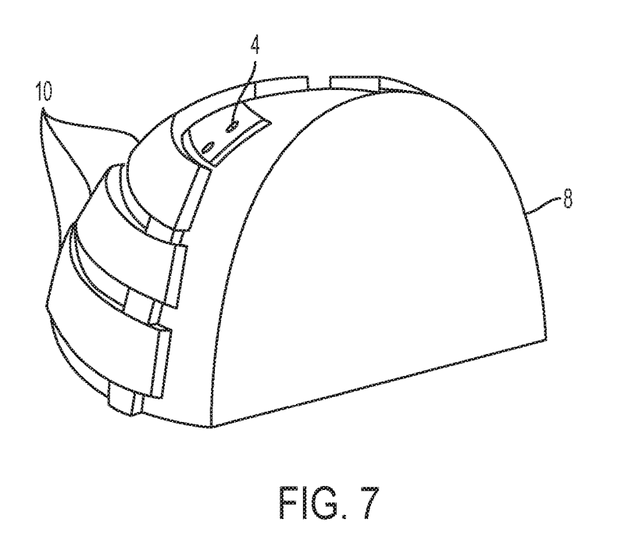
FIG. 7 is a view of a completely screwed implant (bone strip on stabilizer elements) on a frontal module.

The adhering bone strips 10 are then screwed to the plate of absorbable stabilizer elements 4 located therebelow (FIG. 7).

Figure 8:
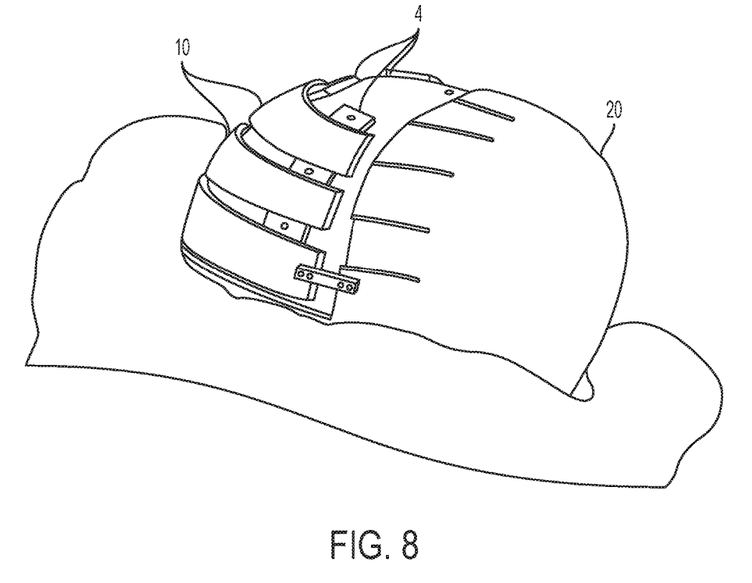
FIG. 8 shows the re-implantation of the re-shaped frontal segment into the prepared site.

Finally, the completely re-shaped and stabilized calotte section 10 is inserted into the site, with fine matching by short heating of the plates 4, and screwed to the remaining calotte 20 (FIG. 8).

Figure 9:
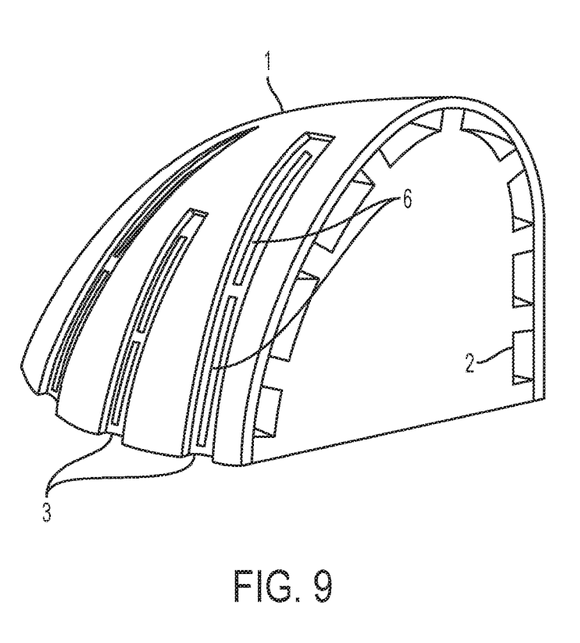
FIG. 9 is a view of a molding shell 1 detachably resting on an interior supporting element 2.

Description of a Particularly Preferred Embodiment of an Inventive Three-Dimensional Model Molding shell A preferred embodiment of the inventive three-dimensional model of the type illustrated in FIG. 9 comprises at least one molding shell 1 resting detach-able on an interior supporting element 2. The outside dimensions of the molding shell are reduced by 1 to 5 mm, preferably 3 mm, in correspondence with the thickness of the bones. Regular grooves or recesses 3 are formed therein for receiving various stabilizer elements 4. The recesses 3 present slot-shaped openings 6 permitting access to stabilizer elements inserted into the recesses 3 from the interior of the shell. The molding shell comprises at least one of a frontal part, a parietal part and an occipital part, which may be present individually and separately from each other or in a form connected to each other. In a particularly preferred embodiment, the parietal part and the occipital part are connected to each other so as to create a parietal and occipital element (parieto-occipital module).

Body The molding shell 1 rests—detachably—on an interior supporting element 2. The supporting element is a frame-like structure in a preferred embodiment.

Stabilizer Elements

Figure 10:
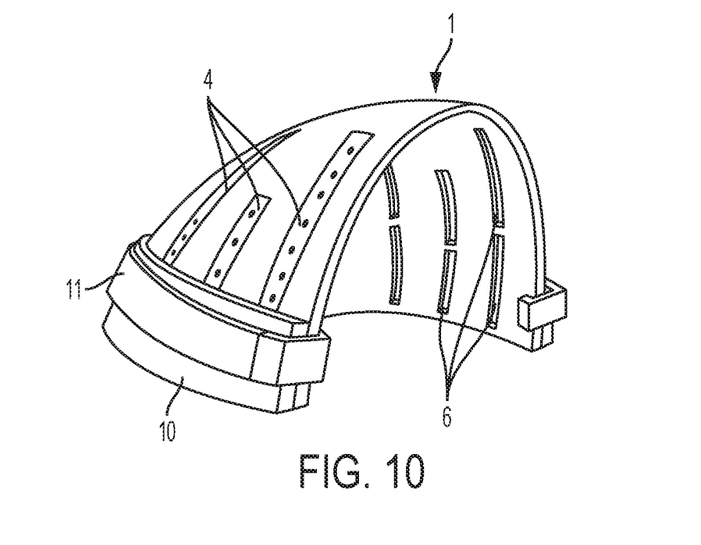
FIG. 10 shows the bone fragments 10 with stabilizer elements 4, which are molded onto the molding shell and which are maintained in their position by means of a fixing means 11, here an elastic tape.

The grooves or recesses 3 of the shell are now clad, as desired, with stabilizer elements 4 moldable in heated condition, as is also shown in FIG. 10. In variation from the so far common surgical technique, the dysplastic bone is now divided into strips and destabilized. The bone stripes may be regularly divided, depending on the necessary degree or kind of correction. The individual strips are molded onto the model and held in their position by means of an elastic tape 5.

Subsequently, the shell is removed while the stabilizer elements are screwed or riveted in a stable manner through the slot-shaped interior openings 6 to the bone strips 10.

The completed implant is then removed from the shell, subjected to fine fitting and implanted as a single block.

The features of the invention, which are disclosed in the foregoing description, in the claims and in the drawings, in their various embodiments, both separately and in any combination whatsoever, may be essential for the realization of the invention.

The invention claimed is:

1. A method for the surgical treatment of cranio-synostosis, comprising the steps of:
    a. manufacturing a three-dimensional sterilizable or disposable model by measuring age-related shape characteristics of a child's skull from the group of features including the horizontal curvature of the forehead, the vertical curvature of the forehead, the width of the forehead, the fronto-nasal angle, the fronto-occipital diameter, the biparietal diameter and the horizontal radius of curvature of the occipital module, selecting one or more of the established features of the measured age-related shape characteristics, conversion of the selected features in manufacturing a three-dimensional sterilizable or disposable model of a child's skull or parts from the skull from the selected features wherein the manufactured model is a moulding shell which comprises at least one of a frontal part, a parietal part and occipital part, which are present individually and separately from each other or connected to each other,
    b. removing a dysplastic calotte section of a patient affected by cranio-synostosis and dividing said calotte section into fragments,
    c. molding said fragments of said dysplastic calotte section of the patient onto said three-dimensional model by thinning, destabilization and/or modeling,
    d. fixing said fragments with stabilizer elements, thus forming an implant consisting of fragments and/or stabilizer elements, and
    e. implanting said implant by fitting and fixing in the patient's skull.

2. The method according to claim 1, wherein said three-dimensional model is reduced by 1 to 5 mm in terms of its exterior dimensions, in correspondence with the thickness of the hone to permit implantation of the re-shaped bone fragments in due form.

3. The method according to claim 1, wherein for molding said fragments of said dysplastic calotte section onto said three-dimensional model, these fragments are placed on said three-dimensional model and are maintained in their position by the application of force, preferably by means of a reversibly removable fixing means, preferably using a resilient tape.

4. The method according to claim 3, wherein said implant is lifted off said three-dimensional model for implantation.

* * * * *